(12) United States Patent
McColskey et al.

(10) Patent No.: US 9,188,519 B2
(45) Date of Patent: Nov. 17, 2015

(54) MULTIPLE SPECIMEN TESTING

(71) Applicants: Joseph David McColskey, Broomfield, CO (US); Andrew J. Slifka, III, Lakewood, CO (US); Elizabeth S. Drexler, Boulder, CO (US); Marc Dvorak, Golden, CO (US)

(72) Inventors: Joseph David McColskey, Broomfield, CO (US); Andrew J. Slifka, III, Lakewood, CO (US); Elizabeth S. Drexler, Boulder, CO (US); Marc Dvorak, Golden, CO (US)

(73) Assignees: THE UNITED STATES OF AMERICA, AS REPRESENTED BY THE SECRETARY OF COMMERCE, Washington, DC (US); THE NATIONAL INSTITUTE OF STANDARDS AND TECHNOLOGY, Gaithersburg, MD (US)

( * ) Notice: Subject to any disclaimer, the term of this patent is extended or adjusted under 35 U.S.C. 154(b) by 279 days.

(21) Appl. No.: 13/910,356

(22) Filed: Jun. 5, 2013

(65) Prior Publication Data

US 2014/0069203 A1 Mar. 13, 2014

Related U.S. Application Data

(60) Provisional application No. 61/699,350, filed on Sep. 11, 2012.

(51) Int. Cl.
*G01N 3/08* (2006.01)
*G01N 3/32* (2006.01)

(52) U.S. Cl.
CPC .. *G01N 3/08* (2013.01); *G01N 3/32* (2013.01); *G01N 2203/0464* (2013.01)

(58) Field of Classification Search
CPC .... G01N 3/32; G01N 3/08; G01N 2203/0464
USPC ................... 73/799, 808, 809, 810
See application file for complete search history.

(56) References Cited

U.S. PATENT DOCUMENTS

| | | | |
|---|---|---|---|
| 3,937,071 | A | 2/1976 | Slota et al. |
| 4,676,110 | A | 6/1987 | Hodo et al. |
| 5,487,299 | A * | 1/1996 | Williamson et al. ......... 73/12.09 |
| 6,023,980 | A * | 2/2000 | Owen et al. .................... 73/797 |
| 7,505,885 | B2 | 3/2009 | Deobald et al. |

FOREIGN PATENT DOCUMENTS

WO    0163243 A2    8/2001

OTHER PUBLICATIONS

William H. Hart, Corrosion Fatigue Testing of Steels as Applicable to Offshore Structures, ASTM STP 1086, 1990, pp. 54-69, Philadelphia, PA., US.
S.S. Rajpathak, W.H. Hartt, Fatigue Crack Initiation of Selected High Strength Steels in Sea Water, ASM 1988, vol. 3, pp. 323-332, New York, NY., US.

(Continued)

*Primary Examiner* — Lisa Caputo
*Assistant Examiner* — Philip Cotey
(74) *Attorney, Agent, or Firm* — Mark E. Bandy; Rankin, Hill & Clark LLP

(57) ABSTRACT

Systems and methods are described for concurrently applying loads to multiple test specimens. The systems and methods are useful for cyclical tensile loading of specimens such as in fatigue strength evaluations. The systems and methods are also useful for low frequency cyclical loading evaluations.

17 Claims, 7 Drawing Sheets

(56) References Cited

OTHER PUBLICATIONS

A.M. Ermi, R.E. Bauer, B.A. Chin, J.L. Straalsund, Multispecimen Fatigue Crack Propagation Testing, Journal of Engineering Materials and Technology, vol. 103, Jul. 1981, pp. 240-245, Richland, WA., US.
S. Rasool, H.E.N. Bersee, Test set-up for accelerated testing for characterization of long term fatigue behaviour, Faculty of Aerospace Engineering, Delft University of Technology, Delft, The Netherlands.
William H. Hart, A Multiple Specimen Test Technique to Determine Fatigue Crack Growth Rates for Conditions Relevant to Offshore Structures, Florida Atlantic University, pp. 70-83, Boca Raton, FL.

* cited by examiner

MULTIPLE SPECIMEN TESTING

CROSS REFERENCES TO RELATED APPLICATIONS

This application claims priority from U.S. provisional application Ser. No. 61/699,350 filed on Sep. 11, 2012.

FIELD

The present subject matter relates to systems and related methods for concurrently subjecting multiple test specimens to tensile loading, and particularly cyclical loading to evaluate fatigue strength characteristics of the specimens.

BACKGROUND

Acquiring fatigue crack growth rate (FCGR) data at low frequencies and near threshold values of a test specimen's stress intensity factor requires a significant investment in time and equipment. Generally, the total time required to conduct a test can be reduced by increasing the frequency of cyclical loading, but some situations require tests to be conducted at low frequencies. These low frequency tests can occupy a load frame for months. For over four decades, researchers have sought methods to test multiple specimens simultaneously as a means of obtaining test data faster, while performing the tests at an appropriate rate. As early as 1966, Robert E. Little of the University of Michigan proposed fatigue testing thin cantilevered coupons (0.84 mm) with a vibration table at either high frequency (approximately 1,000 Hz) or low frequency (28 Hz). As many as 40 specimens could be tested simultaneously in order to generate statistics to predict lifetimes. This was a simple pass/fail test, in which the specimens were fatigued for $10^6$ cycles and inspected for the presence of cracks.

Fatigue testing in bending was also applied to multiple specimens of bone cement, polymer, and composite. A technique proposed by Kim et al. rotates thin flat specimens with dead weights of varying magnitude on each specimen to generate S-N (Stress versus Cycles-to-failure) curves. The cycle at which a given specimen fails is noted and the test is stopped after $10^6$ cycles. For biological materials an immersion bath could be used.

Similarly, apparatuses described by Imig and Garrett and that of Slota and Wegman were designed to generate S-N curves, as the crack length is not monitored during the course of the fatiguing. Both techniques, however, are designed to test nonstandard specimens in tension. The "specimen" of Imig and Garrett is a titanium alloy (57.2 mm wide by 1220 mm long) studied for use in supersonic transport airplanes with stress concentrations machined into the test sections at specific intervals. After one of the test sections fails, that section is removed, the sheet spliced (bolted) back together, and the test resumed. Their system imposes very complex loading sequences to mimic real-time in-flight conditions. Furthermore, thermal loads and corrosive environments could be accommodated. Slota and Wegman offered no dimensions for their specimen, but it appears to be a flat bar. Further description was limited to an actuation method, which employed air pistons to load each specimen in tension, and an electrical switching mechanism that cyclically activated air pistons.

Ermi et al. in 1981 proposed linking eight miniaturized center-cracked tension specimens and loading them cyclically in tension. The load was applied by cyclically pressurizing helium in a chamber via a bellows at the top of the chain of specimens. The initial fatigue pre-crack (FPC) was varied to generate different starting values of the range of the stress intensity factor ($\Delta K$). The linked specimens were fatigued for a pre-set number of cycles, the crack lengths measured, and fatigue crack propagation (da/dN) curves were compiled from data from all the specimens. Elevated temperature tests were possible with this test system.

Multiple specimen fatigue testing with crack growth monitoring is even less common. Hartt refined his multiple specimen fixture to include crack growth monitoring with direct current potential drop (DCPD). Initially, his system was designed to "run out" the crack, then the test was stopped, the broken specimen removed and replaced with a new or dummy specimen, then fatiguing was resumed, generating S-N data. Eventually, DCPD was added, and additional efforts generated da/dN curves. The loading source over time was the same. A servo-hydraulic actuator was employed to test eight specimens at low frequencies, but the control method changed from load to displacement control. Results on tests that used keyhole CT (compact tension) specimens, constant K (tapered) specimens, and bend specimens have been reported. Tests were conducted in both air and sea water to add an element of corrosion fatigue.

Each of these apparatuses was designed to address very specific issues, such as those relating to materials, environmental conditions, or loading mechanisms. Although satisfactory in many respects, a need remains for systems and related methods in which multiple specimens can be concurrently evaluated and particularly subjected to cyclical loadings such as in fatigue strength testing.

SUMMARY

The difficulties and drawbacks associated with previously known practices and apparatuses are addressed in the present systems and methods.

In one aspect, the present subject matter provides a system for simultaneously subjecting a plurality of test specimens to cyclical tensile loading, each specimen defining at least two apertures separated by a region for crack growth. The system comprises a collection of serially arranged links, and a collection of serially arranged clevises. Each of the links and clevises define noncircular apertures. The system also comprises a collection of load transfer members. The specimens, links, and clevises are arranged so as to define a collection of aperture alignments through which the load transfer members extend.

In another aspect, the present subject matter provides a system for concurrently subjecting a plurality of serially arranged test specimens to tensile loading. Each test specimen defines at least two apertures separated by a region for crack propagation. Each specimen has a first face and a second face oppositely directed from and parallel with the first face. The system comprises a plurality of links including a first set of links serially arranged along the first face of the test specimens and a second set of links serially arranged along the second face of the test specimens. Each link defines at least two apertures. The system also comprises a plurality of clevises including a first set of clevises serially arranged along the first face of the test specimens and between the first set of links and the first face of the test specimens, and a second set of clevises serially arranged along the second face of the test specimens and between the second set of links and the second face of the test specimens. Each clevis defines at least two apertures. The at least two apertures of a clevis of the first set of clevises are aligned with apertures in two adjacent links of the first set of links to thereby define at least two loading sites. The at least two apertures of a clevis of the second set of clevises are aligned with apertures in two adjacent links of the second set of links to thereby define at least two loading sites. The at least two loading sites of the first set of clevises and links are aligned with the at least two loading sites of the second set of clevises and links.

In yet another aspect, the present subject matter provides a method for simultaneously subjecting a plurality of test specimens to tensile loading. Each specimen defines at least two apertures separated by a region for crack propagation. The method comprises arranging the plurality of test specimens in a linear series arrangement. The method also comprises positioning at least one set of serially arranged clevises alongside the plurality of test specimens, each clevis defining at least two apertures. The method also comprises positioning at least one set of serially arranged links alongside the plurality of test specimens, each link defining at least two apertures. The method additionally comprises aligning the apertures of the test specimens, the apertures of the clevises, and the apertures of the links to thereby define a collection of aperture alignments. The method also comprises disposing a load transfer member in each aperture alignment. And, the method further comprises applying tensile loading to at least one of the set of serially arranged links and the set of serially arranged clevises to thereby subject the plurality of test specimens to tensile loading.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

Testing the fatigue crack growth of materials at low frequencies and realistic stress-intensity factors has historically demanded a large investment in time. Performing a test at a frequency less than 1 Hz can take weeks, and if meaningful statistics are needed, two to three months might be necessary to provide one set of data on the fatigue crack growth rate. The present subject matter provides systems and strategies for reducing that time frame by testing multiple specimens simultaneously. For example, the present subject matter systems and methods enable concurrent testing of 10 specimens or more. Utilizing the present subject matter systems, multiple compact tension specimens are arranged in series and testing can be performed according to ASTM Standard E647-11. Furthermore, there is no need to interrupt the fatigue testing of the linked specimens should one or more specimens finish before the other specimens. As explained herein, specimens tested in accordance with the present subject matter generate consistent data of fatigue crack growth rate.

Figure 1:
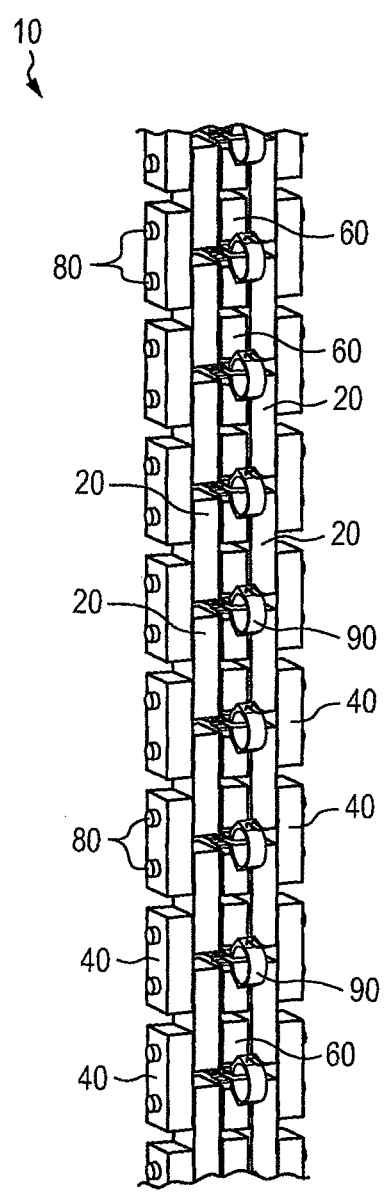
FIG. 1 is a schematic perspective view of a system for concurrently testing multiple specimens in accordance with the present subject matter.

FIG. 1 schematically illustrates a system 10 in accordance with the present subject matter in which a plurality of test specimens can be concurrently evaluated and/or subjected to cyclical loading such as prescribed in testing procedures of ASTM E647-11. Specifically, the system 10 enables concurrent testing of a collection of test specimens 60. The system 10 comprises a plurality of clevises 20 serially arranged along the system 10. A first set of clevises 20 are disposed along a first face of the test specimens 60 and a second set of clevises 20 are disposed along a second face of the test specimens 60. The system 10 also comprises a plurality of links 40 serially arranged along the system 10. A first set of links 40 are disposed along a face of the first set of clevises 20. And a second set of links 40 are disposed along a face of the second set of clevises 20. The system 10 also comprises a plurality of load transfer members 80. In the version of the system depicted in the referenced figures, the load transfer members 80 are in the form of cylindrical pins having circular cross sectional shapes. Each load transfer member 80 extends through apertures defined in two adjacent links 40, two clevises 20, and a test specimen 60. The system 10 may optionally comprise one or more sensors 90 such as sensors or gages for measuring crack mouth opening displacement (CMOD) or crack growth. It will be understood that the present subject matter can be used in conjunction with direct current potential drop (DCPD) for measuring or monitoring crack growth.

Figure 2:
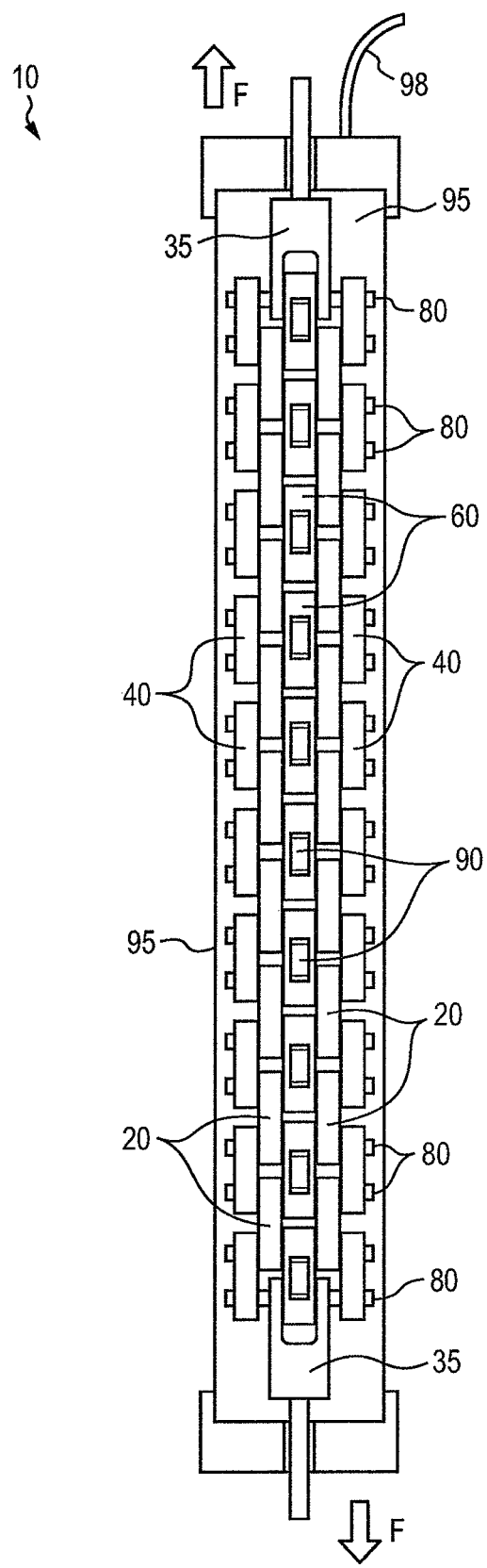
FIG. 2 is a front schematic view of the system depicted in FIG. 1.

FIG. 2 is a front schematic view of the system 10 depicted in FIG. 1. In certain embodiments or applications it may be desirable for the system 10 to include a housing 95 to enclose the plurality of test specimens 60 and expose the specimens 60 to particular environmental conditions such as for example atmospheric agents such as hydrogen or corrosive agents, or conditions such as pressures, temperatures, or combinations of these and/or in conjunction with other factors. One or more conduits 98 can be used to administer gases or other agents to the interior of the housing 95. In certain versions of the present subject matter, the housing 95 is sealed or hermetically enclosed. The system 10 may also comprise one or more, and typically two, main clevises 35. Each main clevis 35 is disposed at an end of the serially arranged test specimens 60 and is engaged or otherwise coupled to a distalmost load transfer member 80.

Referring further to FIG. 2, it will be appreciated that each test specimen 60 is connected to adjacent specimens 60 via two corresponding clevises 20. Upon loading the system 10 in tension, e.g., applying a tensile force F at the main clevises 35, the force is transferred from one specimen 60 to an adjacent specimen 60 so that every specimen 60 in the system 10 is subjected to the same or substantially the same loading condition(s). Serially arranged sets of links 40 on each side of the sets of clevises 20 and test specimens 60, are engaged with each other via the load transfer members 80. The apertures defined in the links 40 are slightly elongated, i.e., noncircular, to allow crack(s) in the specimens 60 to grow a prescribed amount before adjacent links 40 engage one another, as described in greater detail herein. Thus, crack(s) in the specimens 60 are precluded from growing to complete failure, which if allowed to occur, would "break" or result in a discontinuity in the load train. Thus, a loading test of the collection of specimens 60 can continue without interruption even though one or more specimens has developed a fully progressed crack or collection of cracks.

Figure 3:
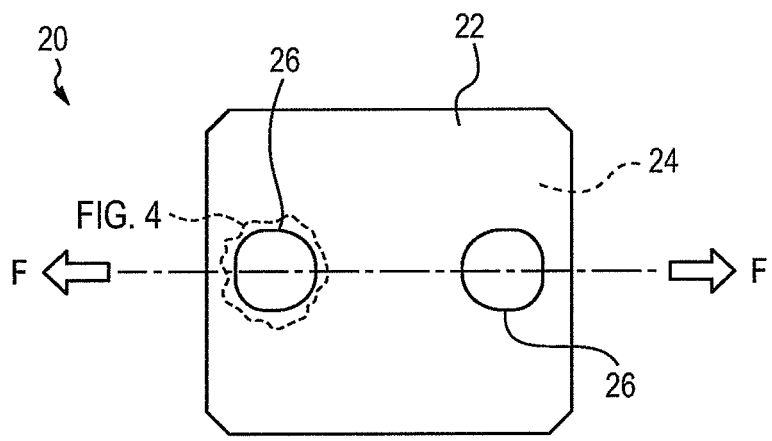
FIG. 3 is a side elevational view of a clevis component used in the system of the present subject matter.
Figure 4:
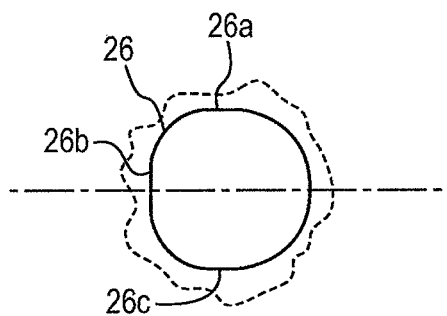
FIG. 4 is a detailed view illustrating a particular configuration for apertures defined in the clevis of FIG. 3.

FIGS. 3 and 4 illustrate a typical clevis 20 and an aperture thereof. Each clevis 20 includes a first face 22, an oppositely directed second face 24, and two apertures 26. Generally, the clevises 20 may be provided in a variety of different shapes, sizes, and/or configurations. However, a square or rectangular shape with beveled corners has been found to be useful. In certain versions of the present subject matter, the apertures 26 of the clevises 20 are provided so as to exhibit a particular configuration. In certain versions, each aperture 26 has a noncircular configuration. More particularly, the noncircular configuration includes one or more nonarcuate or "flattened" regions of the aperture such as shown in FIG. 4, e.g., nonarcuate or linear regions 26a, 26b, and 26c as per ASTM Standard E647-11. For certain versions of the present subject matter, each aperture 26 is configured to include three nonarcuate or linear regions such as shown in FIG. 4. Incorporation of one or more flattened regions and particularly three such regions as depicted in FIG. 4, promotes free, i.e., relatively unrestricted, rotation of the load transfer member 80 inserted in the aperture 26. More particularly, in particular versions of the present subject matter, the clevises 20 utilize particular arrangements of the apertures 26 along the faces 22, 24 of the clevis 20. The apertures 26 of each clevis are defined along the faces 22, 24 such that a plane extending along the direction of application of tensile force F or force vector F (see FIG. 3) bisects each aperture. In certain versions of the present subject matter, two of the nonarcuate or linear regions such as regions 26a and 26c (FIG. 4) are separated from one another by the load line. And, in these particular versions, the load line intersects and more particularly bisects the other nonarcuate or linear region 26b.

Figure 5:
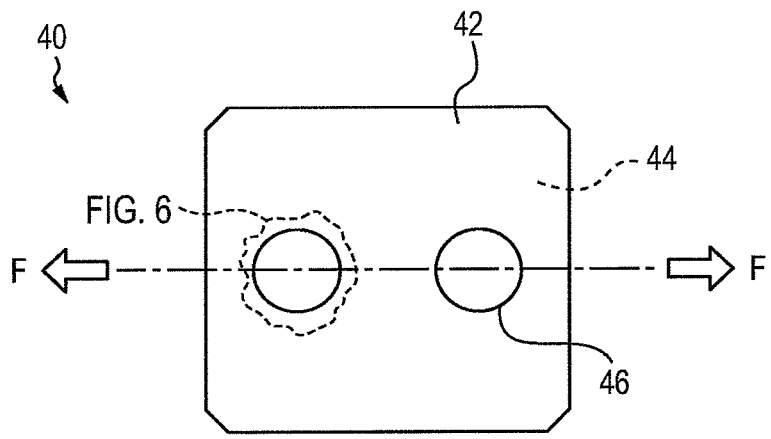
FIG. 5 is a side elevational view of a link component used in the system of the present subject matter.
Figure 6:
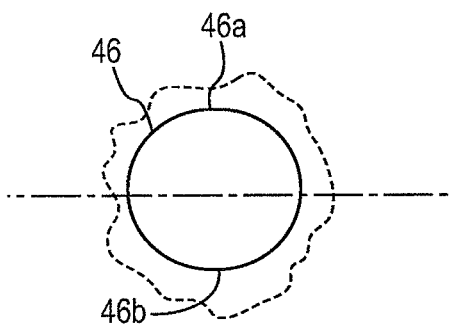
FIG. 6 is a detailed view illustrating a particular configuration for apertures defined in the link of FIG. 5.

FIGS. 5 and 6 illustrate a typical link 40 and an aperture thereof. Each link 40 includes a first face 42, an oppositely directed second face 44, and two apertures 46. Generally, the links 40 may be provided in a variety of different shapes, sizes, and/or configurations. However, a square or rectangular shape with beveled corners has been found to be useful. In certain versions of the present subject matter, the apertures 46 of the links 40 have a particular configuration. In certain versions, each aperture 46 has a noncircular configuration. More particularly, the noncircular configuration has an elongated shape with two linear regions 46a and 46b located opposite from one another which separate two arcuate sides, all of which collectively define the aperture 46. More particularly, in certain versions of the present subject matter, the links 40 utilize particular arrangements of the apertures 46 along the faces 42, 44 of the link 40. The apertures 46 of each link 40 are defined along the faces 42, 44 such that a plane extending along the direction of application of tensile force F or force vector F (see FIG. 5) bisects each aperture. In certain versions of the present subject matter, two of the nonarcuate or linear regions such as regions 46a and 46b are separated from one another by the load line. This arrangement is shown in FIG. 6.

Figure 7:
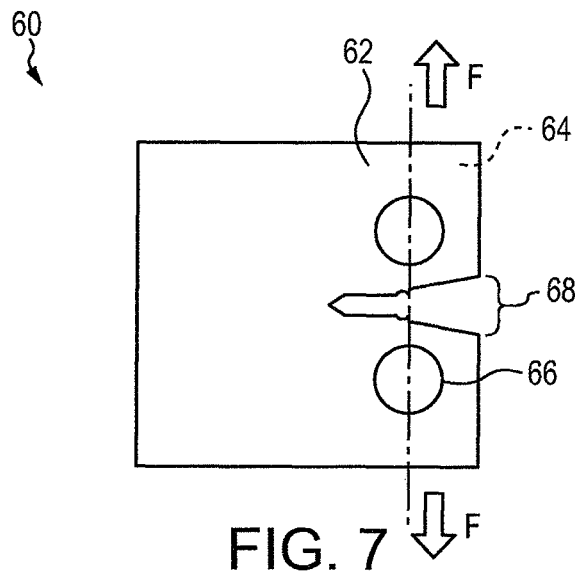
FIG. 7 is a side elevational view of a typical test specimen used in the system of the present subject matter.

FIG. 7 illustrates a typical test specimen 60 which can be used in the system 10. The system defines a first face 62, an oppositely directed second face 64, and two apertures 66. The specimen 60 includes a region 68 for crack propagation generally located between the apertures 66. The apertures 66 of the specimen 60 are aligned along the previously described force vector F. In certain versions, the apertures 66 are circular in shape.

The clevises 20 and the links 40 and their respective apertures, e.g., 26 and 46, are arranged relative to a collection of serially arranged test specimens 60 as follows. The two apertures 26 of a clevis 20 of a first set of clevises, i.e., such as the collection of clevises 20 positioned along a first face 62 of the test specimens 60, are aligned with apertures 46 in two adjacent links 40 of the first set of links. Each set of aligned apertures 26 and 46 thereby form or result in a loading site. As will be appreciated, a load transfer member 80 or pin, is inserted into the aligned apertures 26, 46. Similarly, the two apertures 26 of a clevis 20 of the second set of clevises are aligned with apertures 46 in two adjacent links 40 of the second set of links 40. The resulting aligned apertures 26, 46 define a loading site through which a load transfer member 80 or pin is inserted. The loading sites of the first set of clevises 20 and links 40 are aligned with the loading sites of the second set of clevises 20 and links 40. In particular versions of the present subject matter, a single load transfer member 80 or pin extends through aligned loading sites.

Figure 8:
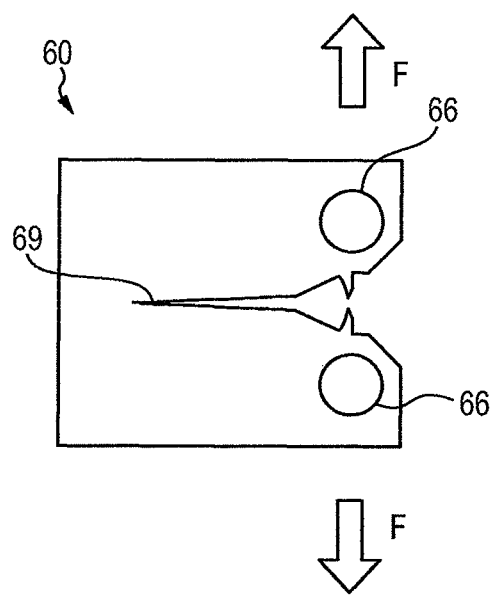
FIG. 8 is a schematic side view of a single test specimen during loading illustrating crack growth.

FIG. 8 illustrates a test specimen 60 after formation and progression of a crack 69 within the region 68 (FIG. 7) for crack propagation. As will be appreciated formation and progression of the crack 69 occurs as a result of tensile loading of the specimen 60 by force vector F generally bisecting the apertures 66. Generally, at least a portion of the clevises are disposed between at least a portion of the links and the test specimens.

Figure 9:
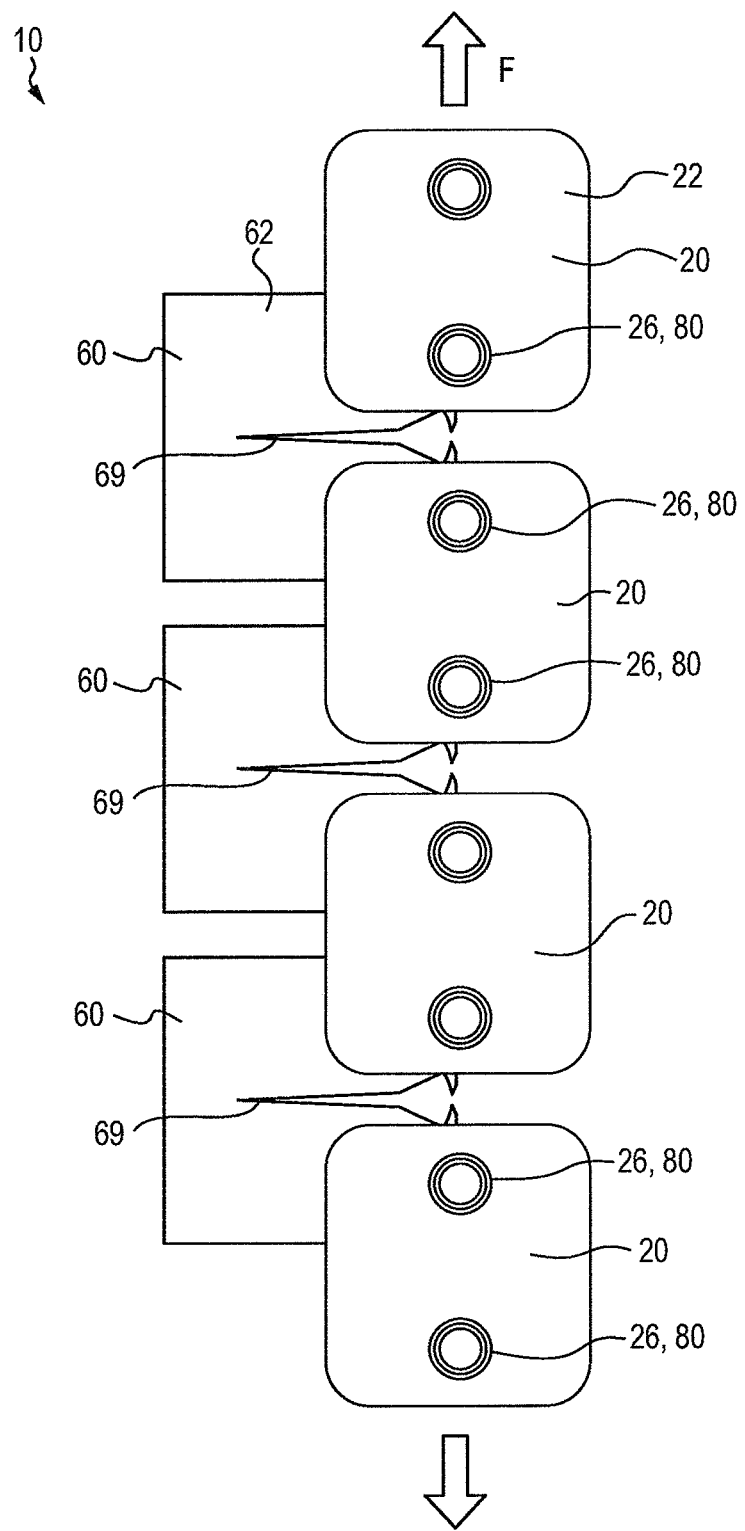
FIG. 9 is a schematic side view of a plurality of test specimens and a plurality of clevises as arranged in a system of the present subject matter during concurrent loading of the specimens.

FIG. 9 is a schematic side view of a plurality of test specimens 60 and a plurality of clevises 20 as arranged in a system 10 of the present subject matter during concurrent loading of the specimens 60. In this particular illustration, each test specimen 60 is shown with a crack 69. For clarity reasons, the links 40, and other components are not shown in FIG. 9.

Figure 10:
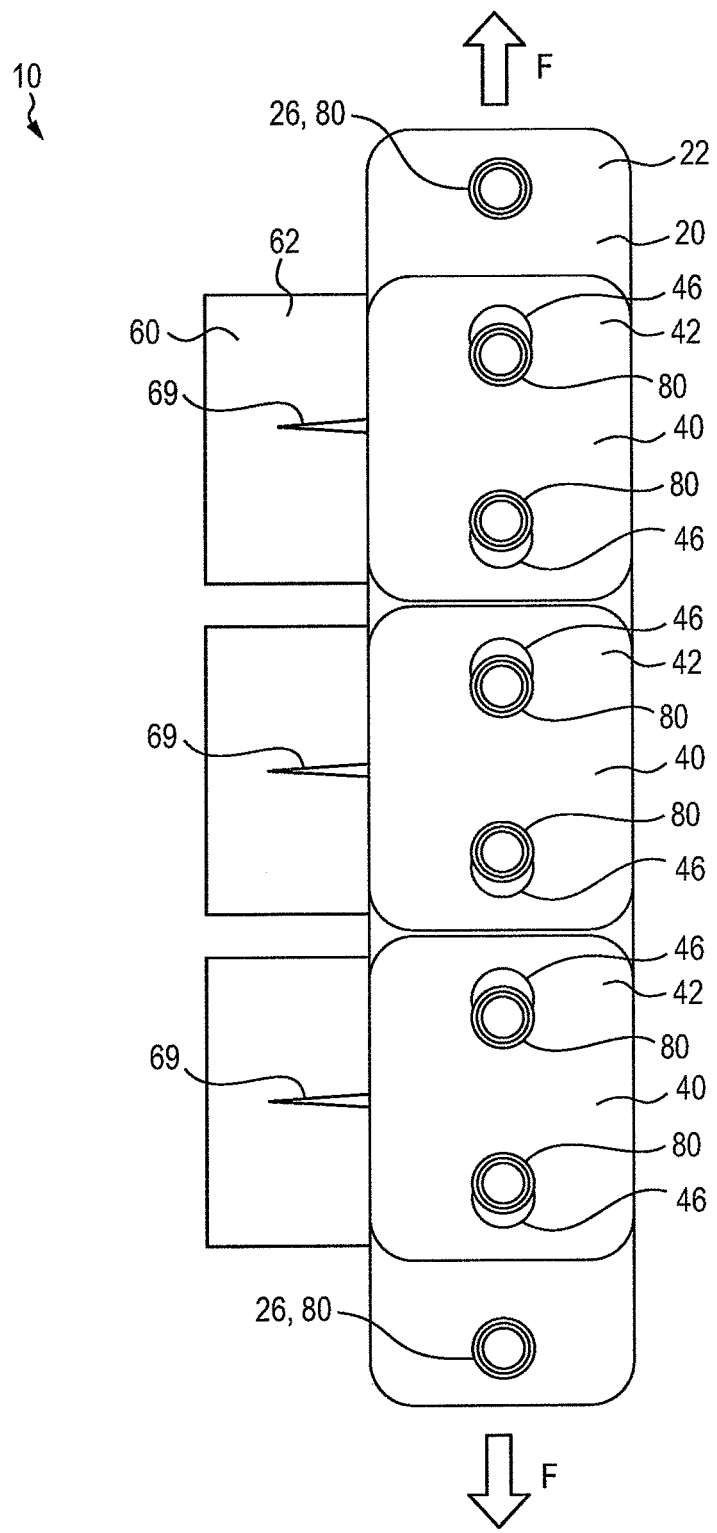
FIG. 10 is a schematic side view of the pluralities of test specimens and clevises depicted in FIG. 9 with a plurality of links as arranged in a system of the present subject matter during concurrent loading of the specimens.

FIG. 10 is a schematic side view of the pluralities of test specimens 60 and clevises 20 depicted in FIG. 9 with a plurality of links 40 as arranged in a system 10 of the present subject matter during concurrent loading of the specimens.

In certain embodiments, the present subject matter also includes the use of supports, spacers, shims, and/or linear displacement or alignment promoters along one or more faces or edges of the test specimens 60, the links 40, and/or the clevises 20. The supports or spacers can be formed from polymeric materials, metals, or composite materials. Additional examples of suitable materials and description of such supports or spacers are provided in the Examples section herein.

The present subject matter also provides various methods. For example, in a particular version of the present subject matter, the present subject matter can be used in low frequency cyclical testing. Nonlimiting frequency ranges are for example from 0.001 Hz to 10 Hz, and more particularly from 0.01 Hz to 1 Hz. Although it is envisioned that most testing evaluations will be performed in tension and will utilize cyclical loading profiles, it is contemplated that noncyclical loadings may be used. Moreover, orientation of the testing system can be vertical, horizontal, or at any angle therebetween. A wide array of testing and evaluation perspectives can be undertaken using the systems and strategies of the present subject matter.

Methods for simultaneously subjecting a plurality of test specimens to tensile loading are also provided. Each specimen defines at least two apertures separated by a region for crack propagation. The method comprises arranging the plurality of test specimens in a linear series arrangement. The method also includes positioning at least one set of serially arranged clevises along side the plurality of test specimens. Each clevis generally defines at least two apertures. The method also includes positioning at least one set of serially arranged links alongside the plurality of test specimens. Each link defines at least two apertures. The method also includes aligning the apertures of the test specimens, the apertures of the clevises, and the apertures of the links to thereby define a collection of aperture alignments. The method also includes disposing a load transfer member in each aperture alignment. Testing or evaluation of the plurality of test specimens is performed by applying tensile loading to the set of serially arranged clevises to thereby subject the plurality of test specimens to tensile loading. Upon sufficient crack advancement at least one of the set of serially arranged links will be subjected to load.

EXAMPLES

Hydrogen is one of the fuels under consideration for a clean energy future. For hydrogen to be considered economical, transportation costs must be comparable to those of oil and gas. Therefore, pipelines are the most likely method for transmission and transportation of hydrogen around the country. However, there is a known deleterious effect of hydrogen on the structural integrity of most metals. Consequently, there is a critical need for measuring mechanical properties of pipeline steels in a pressurized hydrogen environment. Regarding fatigue properties, because slower fatigue rates are theorized to allow more time for the hydrogen to migrate to a high stress region, tests at frequencies of 1 Hz or less are needed to more closely simulate the cyclic operation of a pipeline. Furthermore, this temporal aspect is common to other types of environmentally assisted fatigue.

A research project to measure fatigue crack growth rates (FCGR) of pipeline steels proposed for use for the transportation of hydrogen gas was performed. The test matrix comprises four pipeline steels of two different grades, each from a different source. The steels were selected to offer a comparison between steels of different strengths and microstructures. The steels evaluated were X70A, X70B, X52 modern, and X52 vintage pipeline steels. These materials are from a series of steels designated by the American Pipeline Institute where the number corresponds to the specified minimum yield strength in ksi. The steels were fatigue tested in air and in gaseous hydrogen pressurized to either 5.5 MPa or 34 MPa. All the tests were conducted in the transverse orientation (T-L) at a load ratio of R=0.5 and at frequencies of 1 Hz, 0.1 Hz, and 0.01 Hz. The current ASME B31.12 code requires testing at 0.01 Hz to qualify a material for use with hydrogen gas. This code applies to hydrogen piping and pipelines. The slow frequency is required to allow migration of the hydrogen to the crack tip, providing conservative values for FCGR. A triangular waveform is applied to the specimens for dynamic loading.

These tests were conducted in a stainless steel (SS316) pressure vessel that was designed and manufactured specifically for this purpose. The pressure vessel is rated to 34 MPa, has an inner diameter of 127 mm, and an inner length of 813 mm. The end caps have electrical feed-throughs that permit acquiring the signal from the gages of crack mouth opening displacement (CMOD) from each specimen and an internal load cell that more accurately measures the force P experienced by the specimens. In order to maintain the gas pressure within the vessel, polymeric seals were necessary, but they created drag on the pull rod, which in turn affected the load measured outside of the chamber. The applied forces for the tests were controlled by the internal load cell. The forces were applied via a pull rod connected to the actuator of a servo-hydraulic load frame. The specimens used were a standard CT design, W=44.5 mm, with integral knife edges for attaching the CMOD gage. Tests were conducted and the data analyzed according to ASTM E647-11 for a CT specimen design.

Conventional testing strategies, such as ASTM E647-11, test one specimen at a time. Using this strategy, it would have required years to complete 110 fatigue tests at slow rates with initial values of the range in the stress intensity factor ($\Delta K$) around 10 MPa·m$^{0.5}$. However, as described herein, the present subject matter enabled this extensive undertaking to be performed in significantly less time.

An apparatus in accordance with the present subject matter was used. As many as ten CT specimens were linked in series to one another via a set of clevises. The clevises join one specimen to the next. These coupling clevises are in accordance with ASTM E647-11, which requires flattened pin-holes to allow free rotation of the pins. Untreated maraging C250 was used for its strength and resistance to hydrogen embrittlement. This apparatus was designed for slightly sub-sized specimens, necessary to fit into the pressure vessel.

Another component of the present subject matter assembly is the links, a pair of which is connected to the sides of each specimen. The links are a similar size and shape to the clevises. The clevises span from one specimen to the next, whereas the links span across the crack of each specimen. As described herein, the links have slightly elongated holes with round, rather than flattened bottoms. As the crack grows, the CMOD increases. Knowing the elastic modulus of the material being tested, one can calculate the $CMOD_f$ for $0.7*W = a_f$, the final (f) crack length. Each hole is elongated by $0.5*\Delta CMOD_{(f-i)}$, where i represents the initial condition, to allow the crack to grow only that pre-determined distance before the links are engaged, bearing the load and preventing further loading of the sufficiently cracked specimen. The full load, however, continues to be transmitted to other specimens throughout the chain via the clevises and links. Round pins, i.e., pins each having a circular cross-section, are used to connect the specimens, clevises, and links.

In order to accommodate specimens of different thicknesses, spacers made of polytetrafluoroethylene (PTFE) are inserted between the specimens and the clevises. This keeps the clevises straight so that the loading is aligned throughout the specimen chain. Aluminum spacers are placed between the clevises. These keep the chain of specimens erect and centered so that the pressure chamber can be placed over the specimen chain, enabling the end cap of the chamber and pull-rod assembly to be blindly attached. These aluminum spacers could move freely and do not interfere with the load train once the specimens are loaded in tension. Fatigue tests are conducted in tension-tension, as the chain of specimens cannot maintain alignment under compressive loading.

CMOD gages with a sensitivity of 0.001 mm are attached to each specimen via knife edges that are integrally machined into the specimen at the load line. These gages provide continuous data on the progress of the crack propagation.

Proof that the load was transmitted along the chain of specimens was obtained by attaching a calibrated proving ring to the bottom of a chain of specimens. The top of the specimen chain was attached to the calibrated load cell of the servo-hydraulic load frame. The specimen chain was fatigue loaded at a frequency of 1 Hz, and a load ratio R=0.5, while monitoring the maximum and minimum loads realized by the proving ring. The load values of the proving ring agreed with those of the load cell to within <2% when the weight of the chain is ignored.

Data were acquired through the use of a procedure written in a software that is part of the control software for the servo-hydraulic load frame. Data including time, segment, force, displacement, and output for each CMOD gage, were acquired every 200 cycles over a duration of 5 cycles, approximately 1000 data points per set. A linear regression was fit to the 1000 data points for the CMOD and the internal force. Data outside two standard deviations were excluded as electrical noise. The slope of force (P) versus $CMOD_{i=1-10}$ for the five cycles was used for the compliance when calculating a/W to solve for K and crack length, rather than the maximum values of P and v (CMOD), as called for in FIG. A1.4 in the standard, ASTM E647-11. This was because variables, such as temperature, humidity, and drift, may over time affect the absolute value of the CMOD, but the change in CMOD (ΔCMOD) over a given cycle should not be influenced by anything other than the crack length.

The time savings realized by running multiple specimens simultaneously may be more than simply multiplicative. In the case of the previously described tests, two days of purging in ultra-pure helium and hydrogen gas are preferred to remove all impurities from the vessel and pressurization system. The time is approximately the same whether for one specimen or ten. Furthermore, a considerable amount of expensive, research-grade gases are saved since the volume of the ten specimen vessel is only six times that of a single specimen vessel. The actual test time is dependent on several factors. The thickest specimen of any given material and pre-crack length will theoretically take the longest to complete, no matter how quickly thinner specimens might finish. This data is necessary to populate the lower values of ΔK and da/dN. For values of da/dN=1E-5 mm/cycle, it will take 100,000 cycles to grow the crack 1 mm; at 0.1 Hz, therefore, 1 mm of crack growth would take almost 12 days once the crack has re-activated. These tests typically take three weeks to complete, and the thinned specimens take half that amount of time. If, for example, ten specimens of two materials are tested at 0.1 Hz in hydrogen gas, and there are six thin specimens and four full thickness specimens for statistical purposes, the time savings would be 18 days for the purging and 126 days of testing time.

The previously described evaluation is one example of how the present subject matter multi-specimen apparatus may be utilized. The conditions wherein this apparatus would achieve the greatest savings are low fatigue rates, numerous tests needed at the same condition, expensive or controlled environments. Examples of these controlled environments might be at low temperatures such as at 4 K, since liquid helium is becoming more costly, or certain corrosion tests in which there is concern about contaminating the environment. The pressure vessel used for the previously described evaluation was vertically mounted in the load frame, but the linking system could be adapted for a horizontal loading system, if necessary.

Further evaluations were conducted on four different materials to verify operation of the apparatus. Two API-grade X52 steels were tested together, and two API-grade X70 steels were tested together in air at room temperature. Based on Eq. A1.3 from ASTM E647-11, for given values of P, W, and a, ΔK is inversely dependent on the specimen thickness B. Different specimen thicknesses were employed (for example, 75% and 67% of full thickness) to provide different stress levels so that cracks would begin propagating and the specimens would finish at different times.

Results of fatigue tests demonstrated excellent repeatability. Although the data were limited, the precision of the test method was calculated as reported in ASTM E647-11, Section 11.1.1.1, Reference 30 (McKeighan, et al., 2008). At regularly spaced intervals of the Log of ΔK, the mean and standard deviation of the corresponding Log (da/dN) were calculated. The interval spacing (0.02-0.04) and the number of intervals (5-7) was dependent upon the range of overlap among each dataset. From the mean of the standard deviations (SD), the average da/dN variability was calculated as $10^{[4\times(SD)]}$, and was reported in the ASTM Standard as a percentage. As reported in ASTM E647-11, the average intralaboratory da/dN variability for steel was reported as ±20%. The four materials that were tested with this multi-specimen apparatus in air have variability for da/dN of 20%, 20%, 9%, and 44%. For the most part, all the data showed an excellent lack of variability, except for the last material. It had one dataset that had a lower FCGR than the others of that material, which skewed the variability calculation. However, there was no reason to believe that the data were not valid, so they were included in the calculation. The data obtained were from pipeline steels, which are not likely to be as homogeneous as the steel used to determine the variability reported upon in the Standard.

Data was obtained from several evaluations simultaneously conducted with an apparatus in accordance with the present subject matter on the vintage X52 steel in hydrogen gas pressurized to 34 MPa and a frequency of 1 Hz. For purposes of comparison, data was obtained from Sandia National Laboratory on a similar material, tested at a hydrogen gas pressure of 21 MPa and a frequency of 1 Hz. The consistency of the sets of data shows that the testing method of the present subject matter is a reasonable alternative to repeat testing of single specimens under the same conditions. An apparatus in accordance with the present subject matter was utilized to successfully test nine sets each of ten CT specimens from pipeline steels in pressurized hydrogen gas at different pressures and frequencies.

The present subject matter provides systems and methods for measuring the FCGR of metallic CT specimens. Multiple specimens can be tested simultaneously, under the same conditions, according to ASTM E647-11, and the results exhibit excellent repeatability, considering the probable inhomogeneity of these materials. The configuration of the fixture permits an entire set of specimens to continue fatiguing, even after some have achieved the targeted crack length. This saves considerable time and resources when testing under controlled environments, since there is no need, for example, to vent and re-pressurize test gases, re-fill cryogen, or deal with hazardous fluids when a given sample reaches the targeted crack length. All specimens within the chain are exposed to exactly the same environmental and test conditions, eliminating possible variability in gas concentrations or impurities between tests. The present subject matter apparatus allows for great flexibility in the number of specimens to be tested and is compatible with control of the sample environment (for example, carrying out tests in chambers, dewars, or baths).

The apparatus described herein allows fatigue testing of multiple specimens simultaneously, and in accordance with ASTM E647-11. Up to ten CT specimens can be tested under load control. It is contemplated that the apparatuses of the present subject matter can accommodate more than ten specimens. A crack mouth opening displacement (CMOD) gage for each specimen is employed. The test can continue running until all specimens have reached the targeted crack length (a) typically not more than 0.7*W, where W is the width of the specimen according to ASTM E647-11. With proper considerations, the specimens may be tested in controlled, harsh environments.

The present subject matter can be utilized in performing standard fatigue tests. Compact tension is typically the most common specimen design and so the present subject matter is readily applicable to such. In standard fatigue tests, evaluations are typically conducted at frequencies of 10 Hz to 20 Hz. The present subject matter as previously noted herein, is particularly well suited for use in concurrently testing multiple specimens. The present subject matter can be used in nonstandard test methods and/or with nonstandard test specimens. The present subject matter will find wide application in numerous fields and industries. For example, the present subject matter can be utilized to evaluate material properties of assemblies or components of bridges, buildings, dams, dam gates, turbines, pipelines, valves, transportation assemblies or structures, wind or wave bearing structures, and pumps.

Many other benefits will no doubt become apparent from future application and development of this technology.

All patents, applications, standards, and articles noted herein are hereby incorporated by reference in their entirety.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A system for simultaneously subjecting a plurality of test specimens to cyclical tensile loading, each specimen defining at least two apertures separated by a region for crack growth, the system comprising:
    a collection of serially arranged links;
    a collection of serially arranged clevises;
    wherein each of the links and devises define noncircular apertures; and
    a collection of load transfer members;
    wherein the specimens, links, and clevises are arranged so as to define a collection of aperture alignments through which the load transfer members extend and upon tensile loading, crack(s) in the specimens are precluded from growing to complete failure.

2. The system of claim 1 wherein the load transfer members are cylindrical in shape and exhibit a circular cross section.

3. The system of claim 1 further comprising a plurality of gages or sensors for measuring crack mouth opening displacement or crack growth of the specimens.

4. The system of claim 1 wherein the plurality of test specimens are serially arranged, each specimen defining a first face and an oppositely directed second face, the collection of serially arranged links including a first set of serially arranged links disposed alongside the first faces of the specimens, and a second set of serially arranged links disposed alongside the second faces of the specimens.

5. The system of claim 1 wherein the plurality of test specimens are serially arranged, each specimen defining a first face and an oppositely directed second face, the collection of serially arranged clevises including a first set of serially arranged clevises disposed alongside the first faces of the specimens, and a second set of serially arranged clevises disposed alongside the second faces of the specimens.

6. The system of claim 1 wherein at least a portion of the clevises are disposed between at least a portion of the links and the test specimens.

7. A system for concurrently subjecting a plurality of serially arranged test specimens to tensile loading, each test specimen defining at least two apertures separated by a region for crack propagation, each specimen having a first face and a second face oppositely directed from and parallel with the first face, the system comprising;
    a plurality of links including a first set of links serially arranged along the first face of the test specimens and a second set of links serially arranged along the second face of the test specimens, each link defining at least two apertures;
    a plurality of devises including a first set of devises serially arranged along the first face of the test specimens and between the first set of links and the first face of the test specimens, and a second set of devises serially arranged along the second face of the test specimens and between the second set of links and the second face of the test specimens, each clevis defining at least two apertures;
    wherein (i) the at least two apertures of a clevis of the first set of devises are aligned with apertures in two adjacent links of the first set of links to thereby define at least two loading sites, (ii) the at least two apertures of a clevis of the second set of devises are aligned with apertures in two adjacent links of the second set of links to thereby define at least two additional loading sites, and (iii) the at least two loading sites of the first set of devises and links being aligned with the at least two loading sites of the second set of devises and links.

8. The system of claim 7 further comprising:
    a plurality of load transfer members, wherein one load transfer member extends through a loading site of the first set of devises and links and also extends through a loading site of the second set of devises and links.

9. The system of claim 7 wherein the apertures defined in the plurality of links are noncircular.

10. The system of claim 7 wherein the apertures defined in the plurality of clevises are noncircular.

11. The system of claim 7 further comprising a plurality of gages or sensors for measuring crack mouth opening displacement or crack growth of corresponding test specimens.

12. A method for simultaneously subjecting a plurality of test specimens to tensile loading, each specimen defining at least two apertures separated by a region for crack propagation, the method comprising:
    arranging the plurality of test specimens in a linear series arrangement;
    positioning at least one set of serially arranged devises alongside the plurality of test specimens, each clevis defining at least two apertures; and
    positioning at least one set of serially arranged links alongside the plurality of test specimens, each link defining at least two apertures;
    aligning the apertures of the test specimens, the apertures of the clevises, and the apertures of the links to thereby define a collection of aperture alignments;
    disposing a load transfer member in each aperture alignment;
    applying tensile loading to at least one of the set of serially arranged links and the set of serially arranged clevises to thereby subject the plurality of test specimens to tensile loading.

13. The method of claim 12 whereby as tensile loading is applied, at least one crack forms in the region for crack propagation.

14. The method of claim 12 whereby the tensile loading is cyclical.

15. The method of claim 14 whereby the cyclical loading is applied at a frequency within a range of from 0.001 Hz to 10 Hz.

16. The method of claim 15 whereby the cyclical loading is applied at a frequency within a range of from 0.01 Hz to 1 Hz.

17. The method of claim 12 whereby after positioning the devises and positioning the links, the devises are disposed between the test specimens and the links.

* * * * *